United States Patent [19]
Holohan et al.

[11] Patent Number: 6,143,775
[45] Date of Patent: Nov. 7, 2000

[54] PROCESS FOR PREPARING PHARMACEUTICAL COMPOSITION CONTAINING A HETEROCYCLIC AMIDE

[75] Inventors: James Joseph Holohan, Macclesfield; Ieuan John Edwards, Congleton, both of United Kingdom

[73] Assignee: Zeneca Limited, London, United Kingdom

[21] Appl. No.: 09/447,414

[22] Filed: Nov. 23, 1999

Related U.S. Application Data

[63] Continuation of application No. 09/114,225, Jul. 13, 1998, Pat. No. 5,993,859, which is a continuation of application No. 08/688,162, Jul. 29, 1996, abandoned, which is a continuation of application No. 08/474,191, Jun. 7, 1995, Pat. No. 5,612,367, which is a continuation of application No. 08/116,781, Sep. 3, 1993, Pat. No. 5,482,963, which is a division of application No. 07/805,421, Dec. 11, 1991, Pat. No. 5,319,097.

[30] Foreign Application Priority Data

Dec. 12, 1990 [GB] United Kingdom .................. 9027014
Jul. 19, 1991 [GB] United Kingdom .................. 9115107

[51] Int. Cl.[7] .................. A61K 31/166; A61K 31/18; A61P 11/06; C07C 307/02; C07D 209/10
[52] U.S. Cl. .................. 514/415; 514/604; 548/507; 564/105
[58] Field of Search .................. 514/415, 604; 548/507; 564/105

[56] References Cited

U.S. PATENT DOCUMENTS 5,294,636  3/1994  Edwards et al. .................. 514/415
5,319,097  6/1994  Holohan .................. 548/507

FOREIGN PATENT DOCUMENTS 199543  10/1986  European Pat. Off. .

OTHER PUBLICATIONS

T.S. Kondra'eva, The Technology of Therapeutic Forms, Meditsina, 1991, pp. 85–88, including translation.

I.M. Rabinovich, The Use of Polymers in Medicine, Leingrad Meditsina, 1972, pp. 16–17, including translation.

Haleblian, J., et al., "Pharmaceutical Applications of Polymorphism", J. Pharmaceutical Sciences, vol. 58, No. 8, Aug. 1969, pp. 911–929.

Primary Examiner—Joseph McKane
Assistant Examiner—Jane C. Osweki
Attorney, Agent, or Firm—Pillsbury Madison & Sutro, LLP Intellectual Property Group

[57] ABSTRACT

The invention provides a pharmaceutical composition comprising a particular physical form of N-[4-[5-(cyclopentyloxy-carbonyl)amino-1-methylindol-3-yl-methyl]-3-methoxybenzoyl]-2-methyl-benzenesulphonamide and polyvinylpyrrolidone. It also provides methods for preparing this physical form, and another physical form of N-[4-[5-(cyclopentyloxycarbonyl)amino-1-methylindol-3-yl-methyl]-3-methoxybenzoyl]-2-methylbenzenesulphonamide useful in the preparation of the first mentioned physical form. The compositions are useful in the treatment of diseases in which leukotrienes are implicated, for example asthma.

2 Claims, 5 Drawing Sheets

PROCESS FOR PREPARING PHARMACEUTICAL COMPOSITION CONTAINING A HETEROCYCLIC AMIDE

This is a continuation of application Ser. No. 09/114,225, filed Jul. 13, 1998 (now U.S. Pat. No. 5,993,859); which is a continuation of application Ser. No. 08/688,162 filed Jul. 29, 1996 (abandoned); which is a continuation of application Ser. No. 08/474,191 filed Jun. 7, 1995 (now U.S. Pat. No. 5,612,367 issued Mar. 18, 1997); which is a continuation of application Ser. No. 08/116,781 filed Sep. 3, 1993 (now U.S. Pat. No. 5,482,963 issued Jan. 9, 1996); which is a divisional of application Ser. No. 07/805,421 filed Dec. 11, 1991 (now U.S. Pat. No. 5,319,097 issued Jun. 7, 1994).

The present invention relates to pharmaceutical agents. More particularly, it relates to a pharmaceutical composition comprising a particular physical form of a heterocyclic amide derivative, to processes for the preparation of this physical form, and to another physical form of the heterocyclic amide useful in the preparation of the first-mentioned physical form.

European patent application publication number EP-A2-0199543 discloses certain heterocyclic amide derivatives which antagonise the pharmacological actions of one or more of the arachidonic acid metabolites known as leukotrienes, for example $C_4$, $D_4$, and/or $E_4$, which are known to be powerful spasmogens (particularly in the lung), to increase vascular permeability and have been implicated in the pathogenesis of asthma and inflammation (see J. L. Marx, Science, 1982, 215, 1380–1383) as well as of endotoxic shock (see J. A. Cook, et al., J. Pharmacol. Exp. Ther., 1985, 235, 470) and traumatic shock (see C, Denzlinger, et al., Science, 1985, 230, 330). The compounds are thus useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic aczema, psoriasis, as well as vasospastic cardiovascular disease, and endotoxic and traumatic shock conditions.

One of the heterocyclic amide derivatives disclosed in EP-A2-0199543 is N-[4-[5-(cyclopentyloxycarbonyl)amino-1-methylindol-3-ylmethyl]-3-methoxybenzoyl]-2-methylbenzenesulphonamide. This compound is described in Example 105 of the patent specification, and will be referred to hereinafter as compound 1.

In recent clinical trials compound 1 has been found to be effective in the treatment of asthma when administered orally to asthmatic patients. This ability of compound 1 to be effective when administered orally is unusual and highly desirable.

The pharmaceutical composition used in the aforementioned clinical trials was not entirely satisfactory, and an improved formulation has been sought. As will be described in more detail hereinbelow, a number of technical problems needed to be solved in order for such a composition to be obtained.

Compound 1 has been found to possess relatively poor solubility in water. There has therefore been a need for a pharmaceutical composition suitable for oral administration which comprises compound 1 in the solid state.

It has been found that compound 1 can be obtained in the solid state as a material having a range of different physical properties, depending upon the way in which it has been isolated and subsequently treated. This ability has been found to be due to the fact that compound 1 can exist in more than one physical form, at least one of which has poor physical stability, and which physical forms can be obtained in mixtures. It has also been found that different samples of compound 1 in the solid state have different bioavailabilities.

It is unattractive to develop a formulation containing a mixture of physical forms of a compound that have different bioavailabilities, especially where one is physically unstable, because the effective dose of the compound cannot be properly controlled. There has therefore been a need to find methods for preparing physical forms of compound 1 substantially free of other physical forms.

Methods for preparing three physical forms of compound 1 substantially free of other physical forms have been found, and the physical stability and bioavailability of these three forms have been investigated. Two of these forms, referred to hereinafter as forms B and X, have been found to be physically stable, but to have relatively poor bioavailability. The third of the three forms, referred to hereinafter as form A, has been found to have relatively good bioavailability. However, it has been found that this physical form tends to convert into form B in the presence of water. This property is disadvantageous for a material which is intended to be formulated in a solid composition, because granulation involves the use of water as an adjuvant in the mixing process. Indeed the tablets used in the aforementioned clinical trials were prepared by the wet granulation method from form A, and were found to contain form B in an amount varying from about 25 to about 30% by weight, based on the weight of compound 1.

There is therefore a need for a pharmaceutical composition suitable for oral administration which comprises compound 1 in one physical form, substantially free of other physical forms, which composition is physically stable, can be prepared reproducibly and has good bioavailability.

Surprisingly, it has now been found that pharmaceutical compositions meeting these requirements may be obtained by selecting form A as the active ingredient and polyvinylpyrrolidone as a co-ingredient.

Accordingly the present invention provides a pharmaceutical composition, which comprises, as active ingredient, a physical form of N-[4-[5-(cyclopentyloxycarbonyl)amino-1-methylindol-3-yl-methyl]-3-methoxybenzoyl]-2-methylbenzenesulphonamide (hereinbefore refereed to as form A) substantially free of other physical forms which physical form has an infra-red spectrum (0.5% in KBr) having sharp peaks at 1690, 1530, 1490, 1420, 1155, 1060, 862 and 550 $cm^{-1}$, and polyvinylpyrrolidone.

Form A has an X-ray powder diffraction pattern having no discernable peaks, and is therefore amorphous.

It has been found that compositions according to the invention have acceptable physical stability, can be prepared reproducibly and have surprisingly high bioavailability.

Where reference is made in this specification to form A substantially free of other physical forms, it preferably means that at least 90% by weight of the compound 1 present is in that physical form, more preferably at least 95%, for example at least 96%, 97%, 98% or 99%.

The composition according to the invention may be in any conventional form suitable for oral administration, for example in the form of a tablet, capsule, beadlet or powder. Preferably it is in the form of a tablet.

In the composition according to the invention, the active ingredient is conveniently present in an amount of from 1 to 90% by weight, based upon the total weight of the composition, for example from 10 to 50% by weight.

The polyvinylpyrrolidone is conveniently present in an amount of at least 1% by weight, based on the total weight of the composition. It may, together with the active ingredient, account for the total weight of the composition. However, the composition will more usually further comprise at least one pharmaceutically acceptable carrier. For example, the polyvinylpyrrolidone may be present in an amount of from 1 to 20% by weight based on the total weight of the composition, preferably from 2 to 6% by weight.

Examples of suitable pharmaceutically acceptable carriers include, for example, sugar derivatives such as mannitol, lactose, sorbitol, glucose, sucrose, dextrose, fructose and xylitol, and cellulose derivatives such as microcrystalline cellulose, powdered cellulose and hydroxypropylmethlcellulose. Preferably the composition comprises a sugar derivative, especially lactose, and a cellulose derivative, especially microcrystalline cellulose. The amount of sugar derivative present may, for example be in the range of from 10 to 30% by weight based upon the total weight of the composition. The amount of cellulose derivative present may, for example, be in the range of from 25 to 70% by weight, based upon the total weight of the composition.

The composition may further comprise one or more processing adjuvants such as disintegrates, for example croscarmellose sodium, sodium starch glycolate and starch, and lubricants, for example magnesium stearate, stearic acid, talc and powdered vegetable stearine. The amount of disintegrant present may, for example, be in the range of from 1 to 10% by weight based upon the total weight of the composition. The amount of lubricant present may, for example, be in the range of from 0.25 to 2% by weight, based upon the total weight of the composition.

The composition may be prepared by mixing the ingredients according to a conventional method, for example by a granulation process.

According to another aspect, therefore, the invention provides a process for preparing a pharmaceutical compositions which comprises mixing form A substantially free of other physical forms with polyvinylpyrrolidone and water, and drying the resultant mixture.

The quantity of water used will depend upon the type of pharmaceutical composition required (e.g. a tablet, capsule, powder or beadlet) and the nature of any other ingredient to be incorporated in the composition. Conveniently the weight ratio of water to form A used will be on the range of from 0.1 to 100:1.

When the composition is in the form of a tablet, the weight of the tablet may conveniently be in the range of from 25 to 500 mg, such as from 50 to 250 mg, for example from 100 to 200 mg. The tablet may be uncoated or coated. The coating may be a conventional coating and may be applied by a conventional method.

According to another aspect, the invention provides methods for preparing form A substantially free of other physical forms of compound 1.

Accordingly, the invention provides a process for preparing form A substantially free of other physical forms, which comprises heating another physical form of N-[4-[5-(cyclopentyloxycarbonyl)-amino-1-methylindol-3-yl-methyl]-3-methoxybenzoyl]-2-methylbenzene-sulphonamide (hereinbefore referred to as form B) substantially free of other crystalline forms, which physical form is a monohydrate of N-[4-[5-(cyclopentyloxycarbonyl) amino-1-methylindol-3-yl-methyl]-3-methoxybenzoyl]-2-methylbenzenesulphonamide which is crystalline, has an infra-red spectrum (0.5% in KBr) having sharp peaks at 3560, 1690, 1660, 1540, 1440, 1165, 880 and 858 cm$^{-1}$, and an X-ray powder diffraction pattern having peaks at $2\theta=10.0$, 11.2, 14.6, 19.8 and 23.0°, at a temperature in the range of from 90 to 125° C. under reduced pressure.

The dehydration of form B is preferably conducted at a temperature in the range of from 115 to 122° C.

The pressure during the dehydration of form B is preferably not more than 100 mbara, more preferably not more than 50 mbara. For example, the pressure may be in the range of from 5 to 50 mbara.

Form B may be prepared substantially free of other crystalline forms by crystallisation from hot aqueous acetone. In particular, it may be prepared by dissolving a source of compound 1 in aqueous acetone at an elevated temperature, adding more water, and allowing the resultant mixture to cool. Preferably the water is added. rapidly so that the compound 1 initially separates out as an oil. Material prepared in this way has been found to afford form A in a particularly high state of morphological purity.

The crystalline product may be dried at an elevated temperature, for example at about 60° C. or below. If it is desired to start from an impure source of compound 1, it has been found advantageous to triturate this impure source with hot toluene/ethyl acetate prior to crystallisation.

It will be appreciated that if form B is dried at at high temperature, for example at above 60° C., then some conversion to form A may occur. Material prepared by drying form B at a temperature of about 60° C. or below has been found to be substantially free of any other physical forms of compound 1.

Form B is believed to be novel. The invention therefore also provides form B substantially free of other crystalline forms.

The invention also provides another process for preparing form A substantially free of other physical forms of compound 1, which comprises rapidly evaporating the solvent from a solution of compound 1. For example, it may be prepared by spray drying a solution of compound 1.

The solvent may be any liquid substance capable of dissolving compound 1 and of evaporation at a temperature below the melting point of form A. Examples of solvents include ketones, such as acetone, and nitriles such as acetonitrile, optionally in admixture with water. Aqueous acetone has been found to be a particularly suitable solvent.

The temperature at which the solvent is evaporated should be below the melting point of form A. Conveniently it is below 125° C., preferably below 120° C. When using acetone as the solvent, it has been found that a significant amount of crystalline material is obtained if the temperature is below 100° C. Hence, for example, the temperature at which the solvent is evaporated may be in the range of from 100 to 125° C.

The solution of compound 1 is conveniently prepared by dissolving a crystalline form of compound 1, such as form B, in the solvent. A solution prepared in this way will contain a minimum amount of non-volatile impurities.

It will be appreciated from the foregoing that aqueous acetone is a particularly advantageous solvent for use in the preparation of form A substantially free of other physical forms. Indeed it has also been found that the organic solvent content of form A produced via form B using this solution is very low. According to a another aspect therefore, the invention provides a solution of compound 1 in aqueous acetone. The solution may comprise, for example, from 5 to 15% weight of compound 1, preferably from 6 to 13%. The solvent may comprise, for example, from 3 to 9% by weight of water, preferably from 4 to 8%.

The advantageous nature of the compositions according to the invention may be demonstrated by comparing their properties with corresponding compositions in which form A has been replaced with form B or form X, and with a composition comprising form A which contains no polyvinylpyrrolidone.

Form X is a physical form of compound 1 which is crystalline, has an X-ray powder diffraction pattern with specific peaks occurring at 2θ=8.1, 13.7, 16.4, 20.5 and 23.7° and an infra-red spectrum (0.5% in KBr) having sharp peaks at 3370, 1670, 1525, 1490, 1280, 890, 870 and 550 cm$^{-1}$.

Form X may be prepared substantially free of other physical forms by a process which comprises dissolving a source of compound 1 in hot aqueous acetone, reducing the volume of the resultant solution by evaporation, adding toluene and further reducing the volume by evaporation. If it is desired to employ material which is a relatively impure source of compound 1, such material may advantageously be triturated with hot toluene/ethyl acetate prior to the crystallisation step.

Each of the forms A, B and X may conveniently be characterised, for example, by their X-ray powder diffraction pattern alone, or their infra-red pattern alone.

Figure 1:
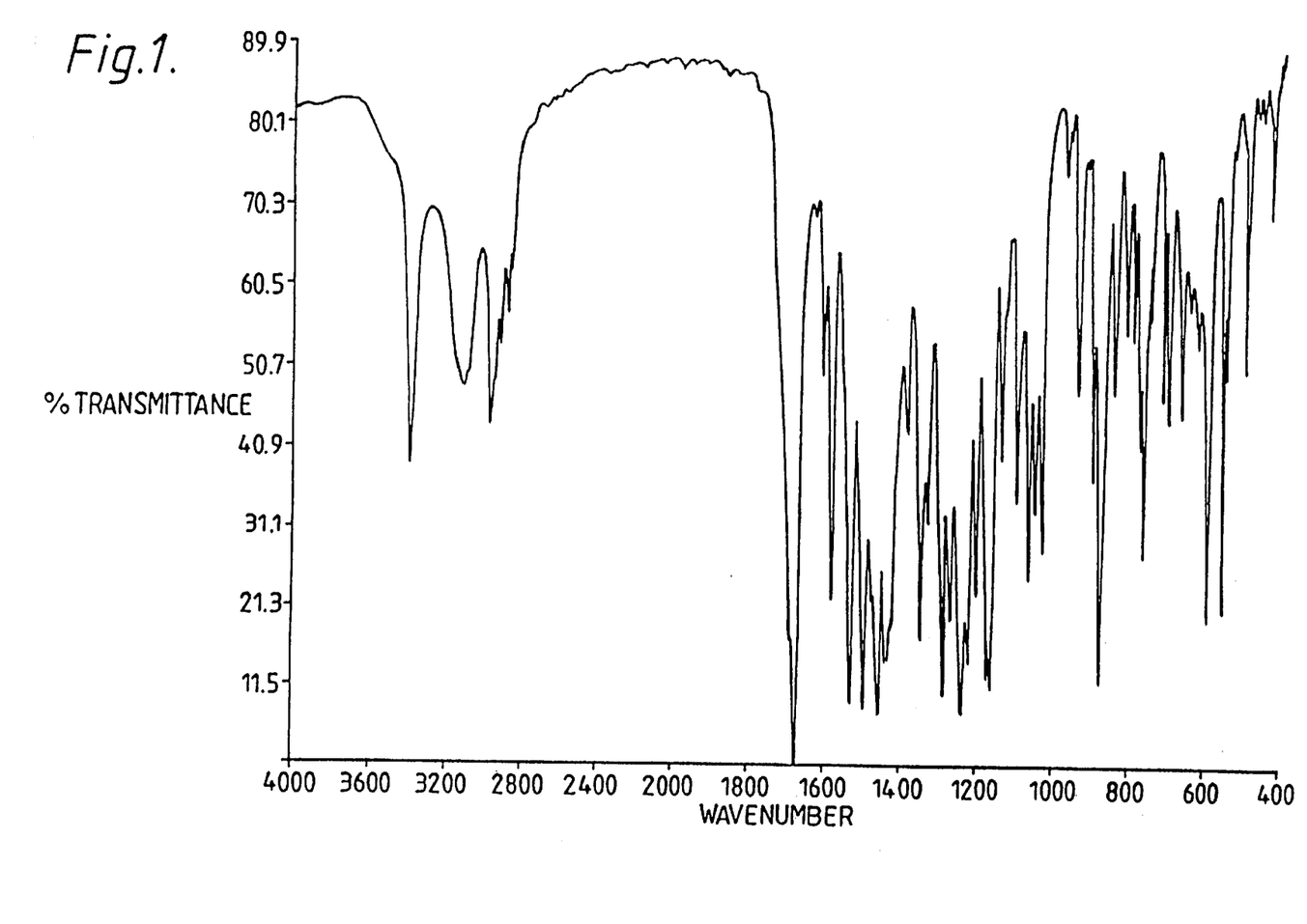
FIG. 1 illustrates an example of an infra-red spectrum for form X.
Figure 2:
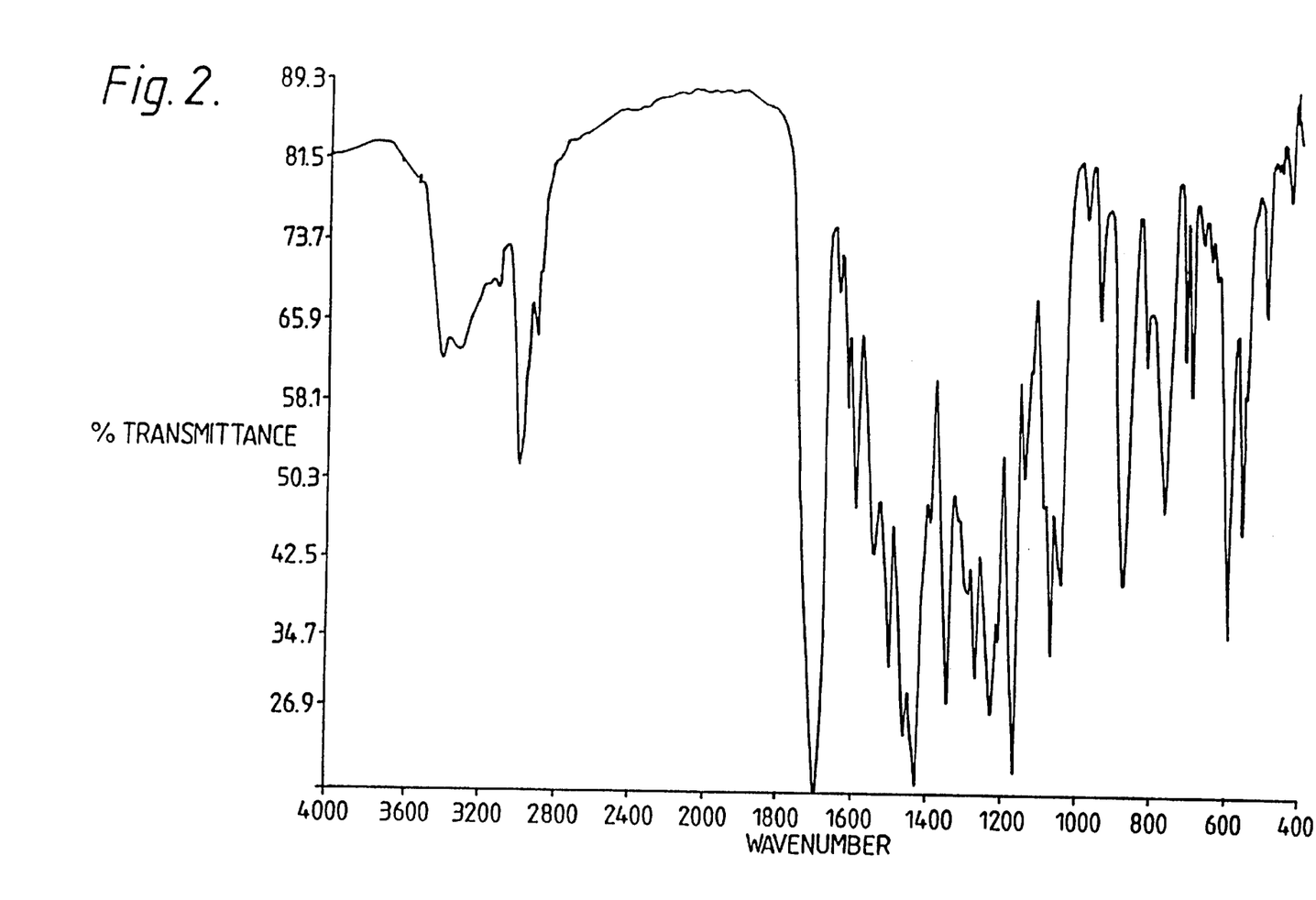
FIG. 2 illustrates an example of an infra-red spectrum for form A.
Figure 3:
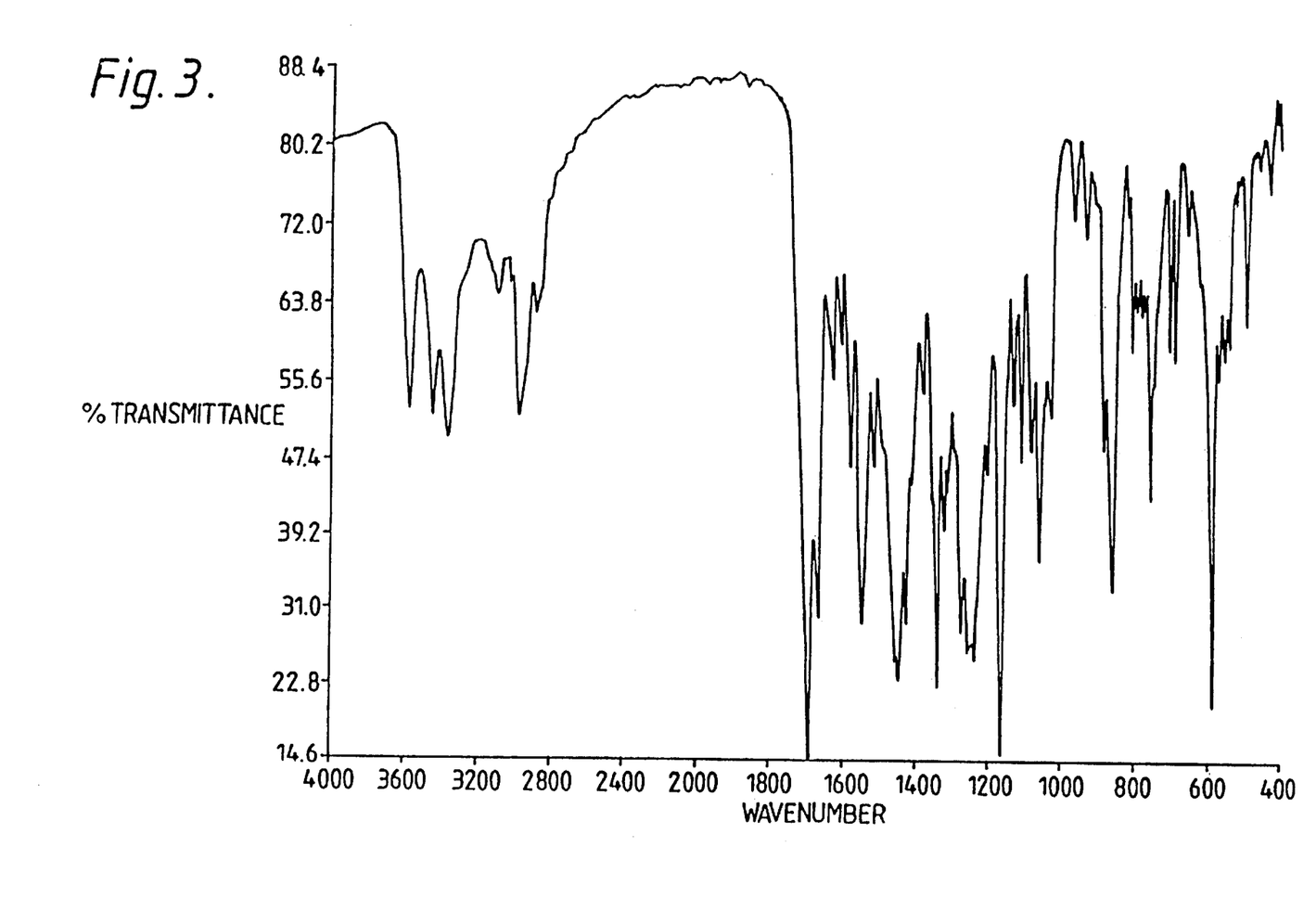
FIG. 3 illustrates an example of an infra-red spectrum for form B.

In this specification, infra-red spectra were determined using a 0.5% dispersion of sample material in a potassium bromide disk over the wave number range 4000 to 400 cm$^{-1}$. Examples of infra-red spectra for each of forms X, A and B are given in FIGS. 1, 2 and 3 hereinafter.

Figure 4:
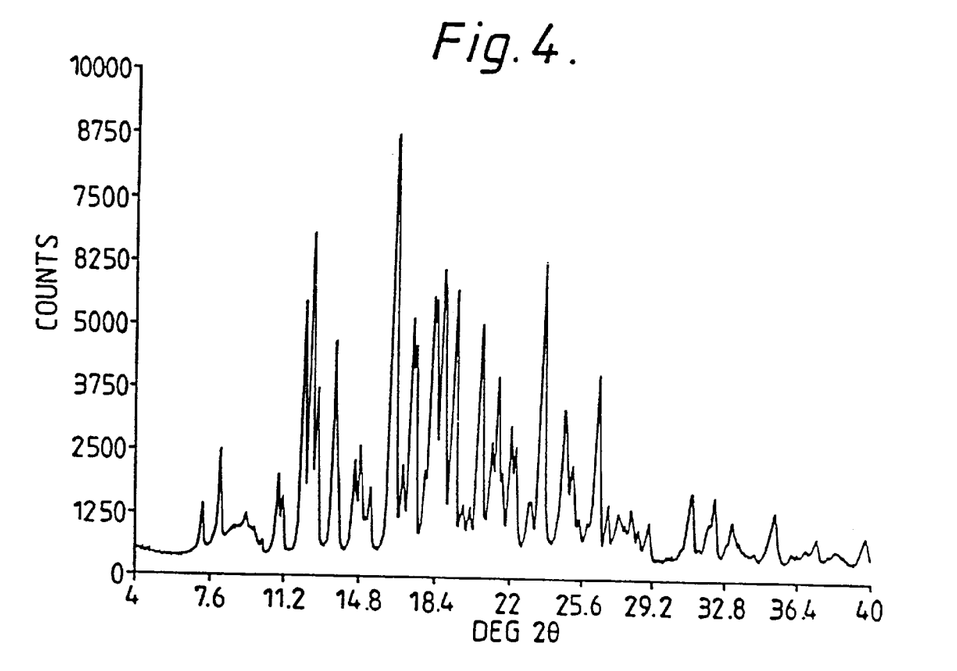
FIG. 4 illustrates an example of an X-ray powder defraction spectrum form X.
Figure 5:
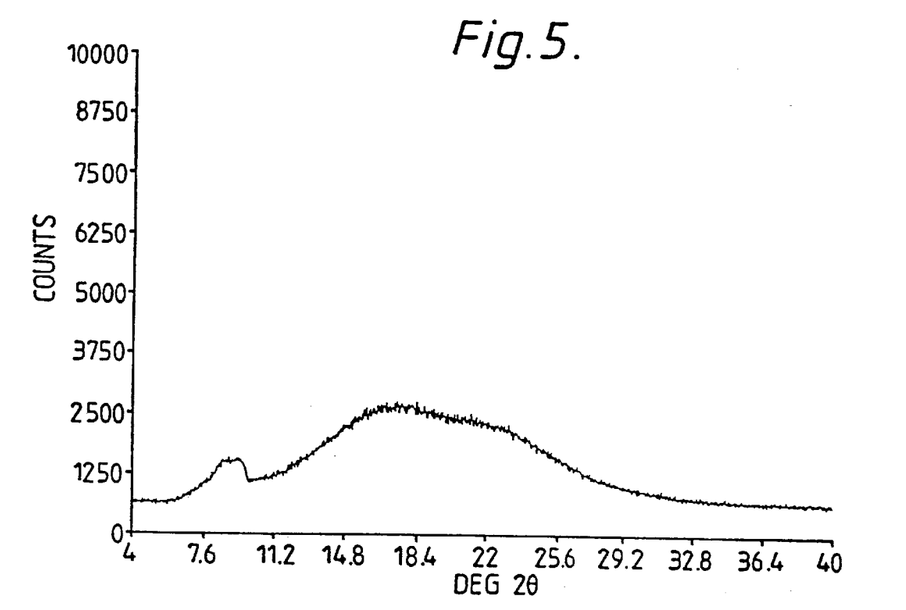
FIG. 5 illustrates an example of an X-ray powder defraction spectrum form A.
Figure 6:
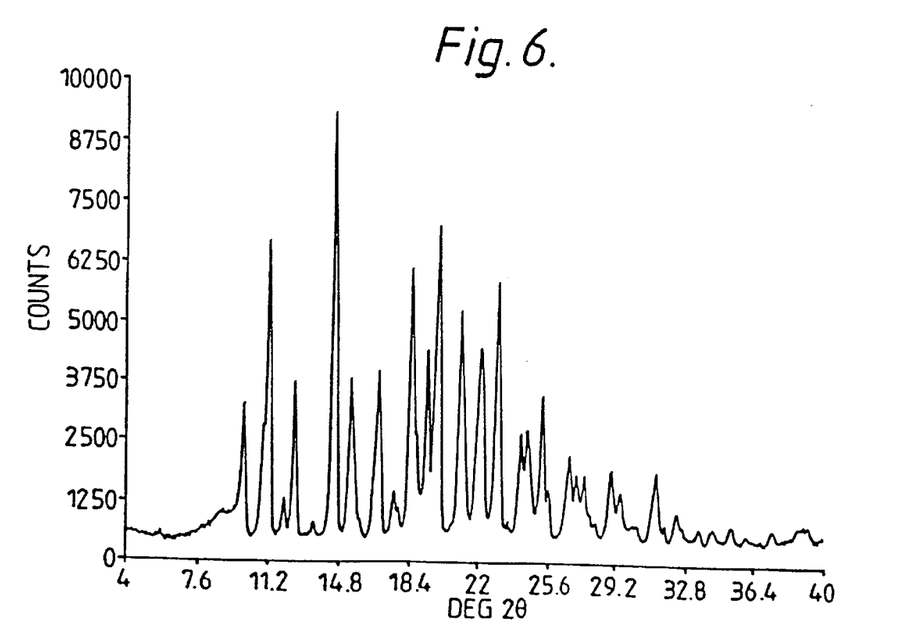
FIG. 6 illustrates an example of an X-ray powder defraction spectrum form B.

X-ray powder diffraction spectra were determined using 2 g of sample material mounted in a Philips standard deep pack holder over the scanning range of 4–40° 2θ counting for 4 seconds per point at 0.02° intervals to produce a trace of spacings against intensity for this range. Examples of X-ray powder diffraction spectra for each of forms X, A and B are given in FIGS. 4, 5 and 6 hereinafter.

The melting points of each of the forms A, B and X generally depend upon their level of purity. Typically, form X has been found to have a melting point of above 190° C., for example about 200° C.; form A between 115 and 140° C., for example about 124 to 132° C.; and form B about 140 to 160° C., for example from 145 to 155° C. Form B has been observed to lose water at a temperature above about 60° C., and may not show a sharp melting point.

As stated hereinabove, form A is acceptably stable in the compositions according to the invention. However, under conditions of high relative humidity and elevated temperatures, conversion of form A into form B has been found to occur. Accordingly, it may in certain circumstances be desirable to keep pharmaceutical formulations comprising form A in the presence of a suitable desiccant, such as silica gel. It may also be desirable to keep them in an airtight container, such as a blister pack.

The dose of compound 1 to be administered to a patient in a composition according to the invention will depend upon the severity of the condition to be treated, the age and the size of the patient. In general, the compound will be administered in a dose in the range of from 0.1 to 10 mg/kg, for example from 0.2 to 5 mg/kg.

Acute toxicity studies have been conducted on compound 1 in order to obtain LD$_{50}$ values. For example, in mice and rats it has been found that the LD$_{50}$ value for compound 1 is >500 mg/kg.

The following non-limiting Examples illustrate the invention.

EXAMPLE 1

Preparation of Form A a) Preparation of an impure source of compound 1

Methyl 3-methoxy-4-(1-methyl-5-nitroindol-3-ylmethyl)-benzoate (prepared as described in Example 4 of EP-A2-0199543) was converted into the free acid by treatment with aqueous sodium hydroxide. The free acid was then converted into the acid chloride by treatment with thionyl chloride in dichloromethane. The acid chloride was then reacted with o-toluenesulphonamide in dichloromethane in the presence of 2.2 equivalents of 4-dimethylaminopyridine to afford the dimethylaminopyridine salt of 4-(1-methyl-5-nitroindol-3-ylmethyl)-3-methoxybenzoyl-2-methylbenzenesulphonamide.

A solution of the dimethylaminopyridine salt of 4-(1-methyl-5-nitroindol-3-ylmethyl)-3-methoxybenzoyl-2-methylbenzene-sulphonamide (30 g) in 2-methoxyethanol (130 ml) and concentrated sodium hydroxide liquor (3.2 ml) was charged to a nitrogen-purged flask containing 10% palladium on charcoal (3.3 g of a 60.9% water-wet paste). The mixture was then stirred under a hydrogen atmosphere at a pressure of 3 bar for 2.5 hours. The mixture was then filtered through diatomaceous earth, and washed through with 2-methoxyethanol (37.5 ml). To the combined liquors was added cyclopentyl chloroformate (9.2 ml), and the mixture allowed to stir under an atmosphere of nitrogen overnight. The temperature was then adjusted to 30–33° C., and 0.8 M hydrochloric acid (68 ml) was added over 20 minutes with vigorous agitation. The mixture was then cooled to 15–20° C. and stirred for one hour. The crude crystalline product was then filtered off, washed with water and dried at 50° C. It was then used in the next step.

b) Trituration of impure compound 1

60 g (0.101 gmol) of the product of step a), toluene 240 ml (4 volumes) and ethyl acetate 150 ml (2.5 volumes) were slowly heated to reflux and 30 ml (0.5 volumes) of distillate were collected to remove most of the released water. The mixture was heated under reflux for one hour (88–90° C.) and was then cooled to 10–15° C. After stirring for three hours at 10–15° C., the solid was filtered through a glass sinter and washed with a 2:1 mixture of toluene (80 ml) and ethyl acetate (40 ml). The product was then dried to constant weight on the sinter to afford 53.2 g of dry compound 1 (yield 91.5%).

c) Preparation of Form B 30.0 g of the product of step b), 210 ml acetone and 12 ml water were charged to a 500 ml reaction flask. The mixture was then heated under reflux for 15 minutes, and was then screened at 45–50° C. through a diatomaceous earth pad on a glass sinter directly into a 500 ml reaction flask. The flask and sinter were washed with a mixture of acetone (60 ml) and water (3 ml). The combined liquids were then stirred in a water bath at approximately 40° C. and water (120 ml) was added over five minutes. The mixture oiled out at first, but then rapidly crystallised. The mixture was then cooled to 20°

C. over one hour, stirred for two hours at 15–20° C. and then filtered. The product was washed with water (60 ml), dried as far as possible on the sinter and then dried in an air oven at 60° C. (max.). The yield of form B was 30.0 g (97%).

d) Preparation of Form A

The product of step c) (15.0 g) was placed in a 500 ml round bottomed flask which was then evacuated on a rotary evaporator at 20 mbar. The flask and contents were then immersed in an oil bath preheated to 118° C., and slowly rotated at this temperature for 6 hours. The mass was broken up on cooling to afford form A as a white powder.

For large scale preparations, form A may be prepared as follows:

30 kg of the product of step c) is spread evenly onto metal trays and heated at 120° C. under vacuum in 7 m$^2$ vacuum oven for up to 24 hours. Typically the pressure is about 20 mbara. On cooling (to 40° C. or below), the material is discharged from the oven and milled to afford the desired form A.

If desired, the form A may be micronised prior to use.

Preparation of Form X

The product of step b) (30.0 g, 0.0521 g mol) was dissolved in acetone (150 ml) and water (4.7 ml) by gentle heating to reflux, and the solution screened through a sintered glass funnel. The filtrate was heated to boiling and 90 ml distillate collected. Toluene (120 ml) was added and a further 75 ml distillate collected. More toluene (120 ml) was added and an additional 75 ml distillate collected. After heating for a further hour at reflux, the mixture was cooled to 15–20° C., and the product collected and washed with toluene (2×30 ml). The yield after drying on the sinter funnel was 29.5 g (98.3%).

EXAMPLE 2

Alternative Preparation of Form A

Form B (which may be obtained as described in Example 1) was dissolved in aqueous acetone to produce an 8% w/w solution of compound 1 in 6% w/w aqueous acetone. This solution was then spray dried using a Niro Laboratory Minor spray drier (obtainable from A/S Niro Atomizer, Gladsaxevej 305, DK-2860 Soeborg, Denmark). The solution was atomised at a flow rate of 2 kg/h with nitrogen at a flow rate of 6.6 kg/h using a two fluid nozzle atomiser. The drying gas used was nitrogen with a flow rate of 70 kg/h and inlet/outlet temperatures respectively of 215/120° C. The form A produced was collected on a bag filter.

EXAMPLE 3

Tablet Formulation of Form A

|  | mg/tablet | mg/tablet | mg/tablet |
|---|---|---|---|
| Granulating Material |  |  |  |
| Active ingredient | 2 | 20 | 50 |
| Croscarmellose sodium NF | 6 | 5 | 5 |
| Polyvinylpyrrolidone USP | 7 | 4 | 8 |
| Microcrystalline cellulose NF | 54 | 74 | 40 |
| Lactose NP | 54 | 50 | 40 |
| Purified Water USP | 80 | 98 | 62 |
| Final Blend Material |  |  |  |
| Dried milled granulation | 123 | 153 | 143 |
| Lactose NF | — | 20 | — |
| Croscarmellose sodium NF | 6 | 5 | 7 |

-continued

|  | mg/tablet | mg/tablet | mg/tablet |
|---|---|---|---|
| Microcrystalline cellulose NF | 69 | 20 | 48 |
| Magnesium stearate NF | 2 | 2 | 2 |

The ingredients of the granulating material were wet granulated. The granules were then dried and milled. The dried milled granulation was then blended with the other ingredients of the final blend mixture and compressed into tablets.

The percentage by weight of form B present, based upon the weight of compound 1 present, was determined by X-ray analysis. For the 20 mg tablet, this was found to be >8%. For the 50 mg tablet more sensitive X-ray methods were used. The percentage by weight of form B before formulation was found to be 3%, and after formulation was found to be >3.2%.

Note: In each of the examples herein, the polyvinylpyrrolidone used had a K value of 29–32. It is believed that any pharmaceutical grade polyvinylpyrrolidone, for example, that having a K value in the range 10 to 100, will be suitable.

EXAMPLE 4

Short Term Stability Test

Tablets prepared according to the method of Example 3 and containing 20 mg of form A were stored under various conditions for 1, 2 and 3 months. The tablets were then studied by X-ray diffraction to determine how much of the active ingredient had been converted into form B. The results are summarised in Table 1 below.

TABLE 1

Stability tests on tablet formulation containing form A

| Storage conditions | % conversion to form B |
|---|---|
| initial | none detectable |
| 1 month, room temp. | none detectable |
| 2 months, room temp. | none detectable |
| 3 months, room temp. | none detectable |
| 3 months, 50° C. | none detectable |
| 1 month, 40° C., 80% RH | 87 |
| 2 months, 40° C., 80% RH | 91 |
| 3 months, 40° C., 80% RH | 82 |

RH = relative humidity

The tablets stored at room temperature and 50° C. were in white high density polyethylene bottles with metal caps.

The tablets stored at 80% RH were exposed to the air.

Comparative Example 1

Tablet formulation of form A containing no polyvinylpyrrolidone.

|  | mg/tablet |
|---|---|
| Granulating Material |  |
| Active ingredient | 50.0 |
| Pregelatinised starch NF | 20.0 |
| Lactose NF | 34.55 |
| Sodium starch glycolate NF | 2.0 |

-continued

| | mg/tablet |
|---|---|
| Microcrystalline cellulose NF | 34.95 |
| Sodium lauryl sulphate NF | 0.5 |
| Purified Water USP | 100.0 |
| Final Blend Material | |
| Dried milled granulation | 142.0 |
| Sodium starch glycolate NF | 6.0 |
| Microcrystalline cellulose NF | 50.0 |
| Magnesium stearate NF | 2.0 |

The ingredients of the granulating material were wet granulated. The granules were then dried and milled. The dried milled granulation was then blended with the other ingredients of the final blend mixture and compressed into tablets.

The percentage of compound 1 present as form B was determined by X-ray analysis before and after granulation. Before granulation it was found that >1.5% of the compound 1 was present as form B. However, after granulation 28% of the compound 1 was found to be present as form B.

These results clearly demonstrate the improved stability of form A in the compositions according to the invention.

EXAMPLE 5

| Capsule Formulation | mg/capsule |
|---|---|
| Active Ingredient | 20 |
| Polyvinylpyyrolidone | 20 |
| Lactose | 177.25 |
| Microcrystalline cellulose | 177.25 |
| Colloidal silicon dioxide | 0.5 |
| Magnesium stearate | 5 |
| Size 0 gelatin Capsule | |

Mix the active ingredient, polyvinylpyrrolidone, lactose and microcrystalline cellulose in a suitable mixer, mix with purified water to proper consistency, dry, size through a suitable milling operation. Mix with the colloidal silicon dioxide and magnesium stearate. Encapsulate with size 0 two piece gelatin capsules.

| Beadlets (spheroids) | mg/capsule |
|---|---|
| Active ingredient | 10 |
| sugar spheres | 200 |
| Polyvinylpyrrolidone | 10 |

Prepare a 10% dispersion of the polyvinylpyrrolidone in purified water. Add the active ingredient and mix until uniformly dispersed; spray onto the sugar spheres using suitable equipment. The beadlets can be filled into size 1 two piece capsules or dispensed in a suitable sachet.

| Powder Formulation | mg/powder |
|---|---|
| Active Ingredient | 20 |
| Polyvinylpyrrolidone | 15 |
| Mannitol | 364.6 |
| Flavour | 0.4 |

Mix the active ingredient, polyvinylpyrrolidone and mannitol in a suitable mixer. Mix to a suitable consistency with purified water, dry, and pass through a suitable sizing operation.

Comparative Example 2

Comparison of the bioavailability of compound 1 in compositions prepared from form A with and without polyvinylpyrrolidone.

24 healthy male human volunteers were randomly assigned to treatment groups. One treatment was a single 50 mg tablet prepared as described in Example 3, and another a single 50 mg tablet prepared as described in Comparative Example 1. During the course of the study each volunteer received both preparations. During each treatment period, blood samples were periodically obtained and the concentration of compound 1 was determined.

| | Product of Example 3 | | Product of Comparative Example 1 | |
|---|---|---|---|---|
| | Mean figure | standard error (I) | Mean figure | standard error (I) |
| Maximum concentration of compound 1 (ng/mL) | 588 | 54 | 223 | 28 |
| Time to maximum concentration (hours) | 2.6 | 0.3 | 3.7 | 0.3 |
| Half-life | 9.0 | 0.5 | 8.2 | 0.7 |
| Area under the curve (ng.h/mL) | 2268 | 220 | 970 | 126 |

These results clearly demonstrate the improved bioavailability of compound 1 in the compositions according to the invention.

Comparison Example 3

Comparison of the bioavailability of compound 1 in compositions prepared with polyvinylpyrrolidone and forms A, B and X.

Tablets containing 20 mg form A, form B or form X were prepared according to the following recipee.

| | mg/tablet |
|---|---|
| Granulating material | |
| Active Ingredient | 20 |
| Croscarmellose sodium NF | 6 |
| Polyvinylpyrrolidone USP | 7 |
| Microcrystalline Cellulose NF | 45 |
| Lactose NF | 45 |
| Final Blend Material | |
| Croscarmellose sodium NF | 6 |
| Microcrystalline Cellulose NF | 69 |
| Magnesium stearate NF | 2 |

Using a balanced crossover design, 8 dogs each received each of the three tablet forms. During each study period, blood samples were periodically obtained from each animal and the concentration of compound 1 determined. The results are summarised below.

| Active ingredient | Maximum concentration ($\mu$g/ml) | Half-life (hours) | Area under curve (ug.h/mL) |
|---|---|---|---|
| Form A | 1.004 | 5.398 | 4.028 |
| Form B | 0.105 | 3.524 | 0.773 |
| Form X | 0.314 | 3.590 | 1.307 |

These results clearly demonstrate the superior bioavailability of compositions according to the invention, compared with compositions containing form B or form X.

What we claim is:

1. A physical form of N-[4-[5-(cyclopentyloxycarbonyl)-amino-1-methylindol-3-yl-methyl]-3-methoxybenzoyl]-2-methylbenzenesulphonamide substantially free of other physical forms, which physical form has an infra-red spectrum (0.5% in KBr) having sharp peaks at 1690, 1530, 1490, 1420, 1155, 1060, 862 and 550 cm$^{-1}$, prepared by a process which comprises spray drying a solution of N-[4-[5-(cyclopentyloxycarbonyl)amino-1-methylindol-3-yl-methyl]-3-methoxybenzoyl]-2-methylbenzenesulphonamide.

2. The physical form of claim 1 wherein the process by which said physical form is prepared comprises spray drying an aqueous acetone solution of N-[4-[5-(cyclopentyloxycarbonyl)amino-1-methylindol-3-yl-methyl]-3-methoxybenzoyl]-2-methylbenzenesulphonamide.

* * * * *